United States Patent [19]
Riederer et al.

[11] Patent Number: 4,504,908
[45] Date of Patent: Mar. 12, 1985

[54] MATCHED FILTER FOR X-RAY TEMPORAL SUBTRACTION

[75] Inventors: Stephen J. Riederer; Norbert J. Pelc, both of Wauwatosa, Wis.

[73] Assignee: General Electric Company, Schenectady, N.Y.

[21] Appl. No.: 358,741

[22] Filed: Mar. 15, 1982

[51] Int. Cl.³ .................... G06F 15/42; G06F 1/02; H04N 5/32
[52] U.S. Cl. .................... 364/414; 358/111; 364/416; 364/722
[58] Field of Search .............. 364/413, 414, 416, 722; 358/111; 378/99; 250/302, 303

[56] References Cited

U.S. PATENT DOCUMENTS 4,064,530 12/1977 Kaiser et al. ................... 358/36
4,204,225 5/1980 Mistretta ..................... 358/111
4,204,226 5/1980 Mistretta et al. ............... 358/111
4,399,457 8/1983 Riederer et al. ................ 364/414
4,449,195 5/1984 Andrews et al. ................ 358/111

OTHER PUBLICATIONS

Robert G. Gould et al., "A Digital Subtraction Fluoroscopic System with Tandem Video Processing Units", Proc. SPIE 273:125, 1981.
Robert G. Gould et al., "Investigation of a Video Frame Averaging Digital Subtraction Fluoroscopic System", Proc. SPIE 314:184, 1981.
Robert Kruger et al., "Time Domain Filtering Using Computerized Fluorography-Intravenous Angiography Applications", SPIE, vol. 314, Digital Radiography, pp. 319-325, 1981.
Robert Kruger, "A Method of Time Domain Filtering Using Computerized Fluoroscopy", Medical Physics, vol. 8, No. 4, Jul./Aug. 1981, pp. 466-469.

Primary Examiner—James D. Thomas
Assistant Examiner—Dale M. Shaw
Attorney, Agent, or Firm—Fuller, House & Hohenfeldt, S.C.

[57] ABSTRACT

A matched filtering method for X-ray image subtraction procedures in which an X-ray contrast medium is injected intravenously. A sequence of pre-contrast X-ray images are made during a period before the medium arrives in a blood vessel that is to be imaged and the sequence is continued through the post-contrast period and in some cases, an after-contrast period. A curve or plot of how projected intensity of the contrast medium varies as a function, h, at times (t) is determined at some prior time based on characteristic patients or, in the alternative, by using the post-contrast image data obtained from the patient presently undergoing examination. In either case a sequence of coefficients or weighting factors are produced that are proportioned to the value of the function h at the time (t) at which the corresponding image in the post-contrast sequence was acquired. By multiplying the coefficients and their time matched images, those images which have more contrast medium intensity get the most weight, which taken in conjunction with some image subtraction steps, results in maximizing contrast medium signal relative to noise and in utilizing all of the contrast medium signal.

29 Claims, 14 Drawing Figures

MATCHED FILTER FOR X-RAY TEMPORAL SUBTRACTION

BACKGROUND OF THE INVENTION

The invention disclosed herein is a matched filter for use in connection with temporal subtraction of X-ray images.

Digital fluoroscopy apparatus and methods are used for visualizing the flow of an X-ray contrast medium through blood vessels. One digital fluoroscopy modality involves projecting an X-ray beam through a body, converting the resulting X-ray image to an optical image with an image intensifier, converting the optical image to analog video signals with a video camera and then digitizing the video signals to form a matrix of digital values that correspond in magnitude to the intensity of the picture elements (pixels) that compose the image. In temporal imaging, an image of a region of the anatomy that contains the blood vessels of interest is obtained before an intravenously injected X-ray opaque medium reaches the vessels. This image is typically stored as a mask image. When the X-ray contrast medium begins to flow through the vessels, a series of live images are obtained. The mask image is then subtracted from the successive live images to produce a sequence of difference images. The object of subtraction is to cancel all image content such as bone and soft tissue which is unchanged in the mask and live images and let the image of the contrast medium containing blood vessels remain for display. As is known, the pre-contrast mask images and post-contrast images will always have some noise content that is introduced by the X-ray system and the electronic components that are used to generate and process the signals that represent the image.

One method that has been used to reduce the effect of noise is to integrate several successive images on the assumption that, since noise is a random phenomena, it will cancel out. Integration over a long period of time is not fully satisfactory, however, because it introduces a greater probability that the body being examined will have moved during the integration interval in which case motion artifacts become evident in the visible image.

Recursive filtering has been proposed for reducing the effect of noise in temporally subtracted X-ray images, that is, in the difference image that results from subtracting a mask image obtained at one time from a live contrast medium exhibiting image obtained shortly thereafter. Recursive filtering in temporal subtraction systems was recently described in several articles: Kruger, R. A. "A Method for Time Domain Filtering Using Computerized Fluoroscopy": Medical Physics, Vol. 8, No. 4, July/August 1981, pp. 465–469; Kruger, R. et al, "Time Domain Filtering Using Computerized Fluoroscopy—Intravenous Angiography Applications", SPIE Vol. 314 Digital Radiography (1981), pp. 319–326; Gould, R. G. et al "Investigation of a Video Frame Averaging Digital Subtraction System", SPIE Vol. 314, pp. 184–190 (1981); and, Gould, R. G. et al "A Digital Subtraction System With Tandem Video Processing Units," SPIE Vol. 273, pp. 125–132 (1981). The apparatus and method described in these articles assumes prior knowledge of the manner in which the concentration of contrast medium in the blood vessels of interest varies with time. Generally speaking, a plot of concentration versus time results in a curve that bears a rough resemblance to a Gaussian distribution curve but, more specifically is usually modeled by gamma variate wherein there is a relatively low concentration of contrast medium when the medium first reaches the blood vessels of interest and then it reaches a peak concentration followed by a decline until the vessel is again occupied by blood that does not contain any contrast medium. By way of example, some contrast medium may be present over an interval of 15 or more seconds whereas, the time of interest existing between the two half-maximum points on the plot may be a 5–10 second interval. Two recursive filter channels are used in the X-ray image subtraction system described in the first two cited articles. Each effectively converts the contrast medium or bolus flow characteristics from the time domain to the frequency domain and the ultimate result of cooperative action between the two filters is to effectuate a band pass filter in whose output signal noise and unchanged pre-contrast and post-contrast structures are cancelled out and an image of the contrast medium containing vessels remains.

The digitized video signals for each pre-contrast and post-contrast image in a sequence are input to the recursive filter channels simultaneously. Each channel has a full-frame memory in which a fractional amplitude portion of the sum of all previous or earlier image frames are added to a fractional amplitude portion of the live or present video signal constituting a frame such that the relative importance of a signal n frames previous is determined by the value of a coefficient "K". For example, if "K" were equal to 0.5 and (1−K) were equal to 0.5, the output signal from a memory would consist of ½ of the present signal, ¼ of the next earlier frame signal, ⅛ of the next earlier frame, 1/16 of the next frame behind that and so on such that the signal 7 or 8 frames preceding the present of live signal has little weight. When a multiplicity of such identical signals are summed, the result is a signal identical to any one of the summed signals and of the same magnitude as the unattenuated incoming live video signal because the sum of "K" and (1−K) is always unity. However, when random noise present in the video signal, which is independent from frame to frame, is summed, it tends to be cancelled or in any case not be reinforced as is the periodic video signal. It can be demonstrated that the improvement in the signal-to-noise ratio with this scheme is equal to 10 log (2−K)/K db.

Thus, if the value of K were 0.5, the value of the fraction would be 3 and the logarithm would indicate a 4.7 db signal-to-noise ratio improvement. Similarly, if K were smaller, such as 0.3, the signal-to-noise (SNR) improvement would be about 7.53 db.

In one recursive filter channel, the video signal is fed through an attenuator that inputs the value of KxL (live video) to a summer. The summer output is an input to a full-frame memory. The output of the full-frame memory is another input to the summer and in this loop, the stored or accumulated video signal is multiplied by (1−K). The other recursive filter channel functions in the same way except that it uses a different coefficient K. The contents of the memories for the common frame in each of the recursive filter channels are then subtracted to produce a net difference image digital frame format. This is reconverted to analog video signals for display on a television monitor.

The imaginative concept of using two recursive filters to achieve a pass band from which noise is excluded has resulted in a significant improvement in SNR over previously known noise reduction schemes for X-ray image subtraction. Applicants, however, recognized that in the described system, noise reduction is to some extent achieved at the expense of useful signal reduction where useful signal is that which represents the X-ray contrast medium. In other words, a two channel recursive filtering system does not use the image representative signals with maximum efficiency. Useful signal is cancelled out by reason of two different values of K being used in the respective filter channels. In reality, this means that the two channels have different time constants. Thus, for a frame obtained at any time along the bolus interval or, in other words, when contrast medium is present in the vessel, the filter with the fastest time constant will have practically no remnant of frames that were taken far back in time whereas the slow time constant filter may still have a significant amount of signal carried over from frames obtained in the more distant past. Moreover, the slow time constant filter, which should theoretically have the data representative of a pre-contrast mask, actually contains some signal that was developed after contrast medium started to pass across the X-ray beam. Thus, when the two images are subtracted some contrast medium signal is cancelled and total contrast medium signal is reduced undesirably.

SUMMARY OF THE INVENTION

A primary object of the present invention is to provide a method and apparatus for X-ray image subtraction that is distinguished by its capability for increasing the signal-to-noise ratio, that is, the signal corresponding to an X-ray contrast medium in the blood vessel relative to the noise in the image of the vessel, while at the same time maintaining the signal representative of the contrast medium at maximum value. A corollary of this object is to overcome the disadvantage of recursive filtering where, when a signal representative of a mask is subtracted from a signal representative of a contrast medium, the useful difference signal is substantially reduced because the image that is subtracted also has some contrast medium contribution in it.

Briefly stated, in accordance with the invention, matched filtering is used. Matched filtering is based on the recognition that the concentration of contrast medium in the vessel is a function of time. The difference image at any moment in time (t), corresponding with a television frame time, for instance, is weighted by a function that corresponds to the manner in which the concentration varies with time. The summation of such weighted frames represents the final difference image. In forming the sum, the original difference images having the largest signal are weighted most heavily to thereby maximize the available signal-to-noise ratio.

The manner in which the foregoing objects and other more specific objects of the invention are achieved will be evident in the ensuing more detailed description of an existing recursive filtering method and the new matched filtering method and apparatus which will now be set forth in reference to the drawings.

DESCRIPTION OF A PREFERRED EMBODIMENT

It will be necessary to describe a known but advanced recursive filtering method in some detail in order to show the advantages of the new matched filtering method.

Figure 1:
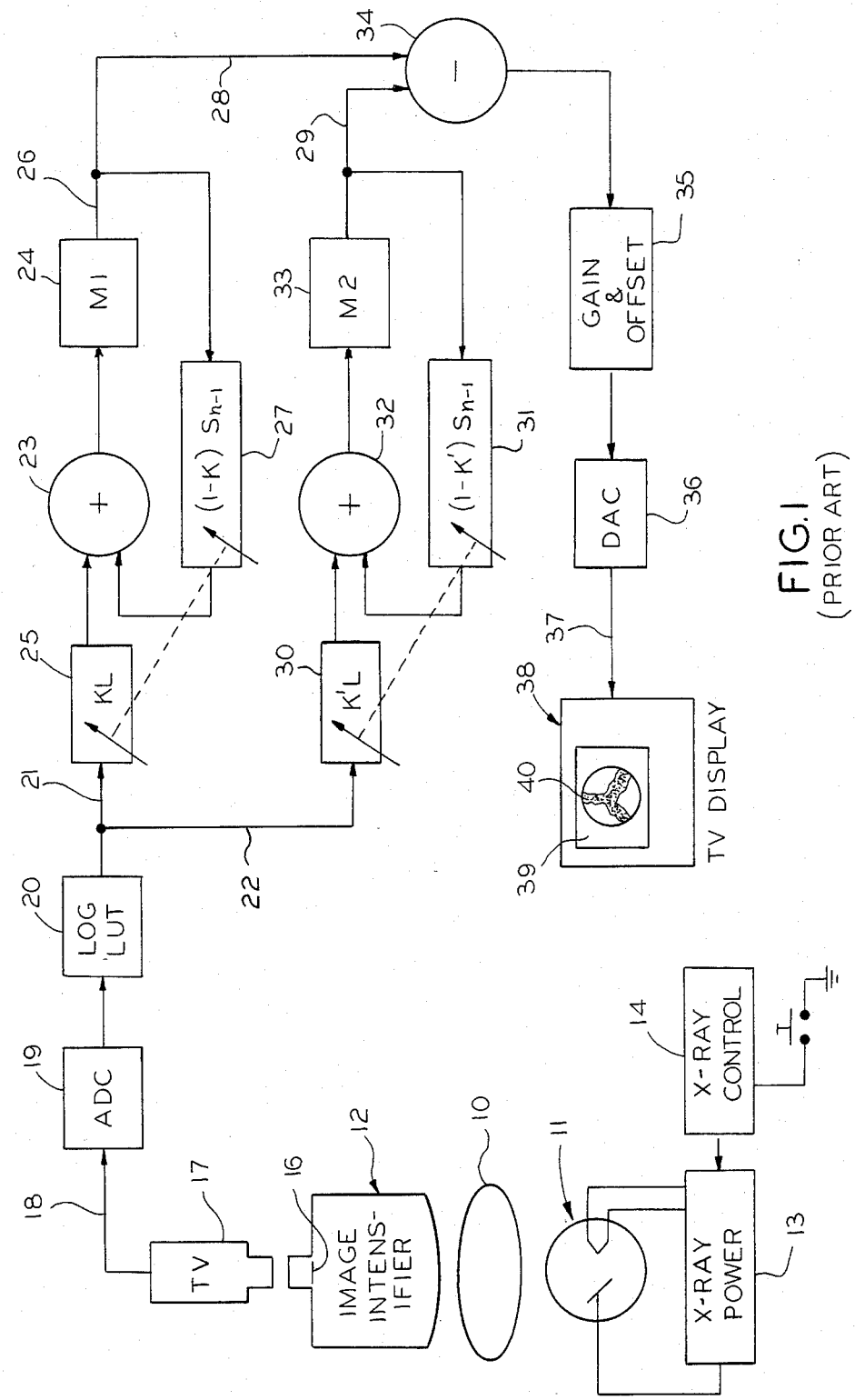
FIG. 1 is a block diagram of an X-ray image subtraction system wherein recursive filtering is used in accordance with the prior art.

An X-ray image subtraction system using recursive filtering is shown diagrammatically in FIG. 1. The body that is to undergo an arteriographic study is represented by the ellipse marked 10. The body is interposed between an X-ray tube 11 and an X-ray image intensifier 12. The X-ray tube is energized from a power supply that is symbolized by the block marked 13. The X-ray power supply is controlled with conventional control circuitry represented by the block marked 14. A manually operated hand switch or foot switch 15 is operable by the user to bring about energization of the X-ray tube. When the X-ray tube 11 is energized, it projects a beam through the body 10 and the emergent X-ray image is inputted to image intensifier 12. The intensifier is conventional in that it converts the X-ray image to an electron image and then to a minified optical image which appears on a phosphorescent screen 16 in the intensifier. The resultant optical image is input to a video or television (TV) camera 17. A cable 18 couples the video camera to an analog-to-digital converter (ADC) represented by the block marked 19. ADC 19 converts the analog video signal output of camera 17 to digital values corresponding in magnitude to the intensities of the picture elements (pixels) that compose the X-ray image.

Generally, for the recursive filtering system shown in FIG. 1, X-ray exposures will be made with a voltage of 55 to 100 kV applied between the anode and cathode of the X-ray tube and with an electron current through the tube having a value of 5–20 mA. In other words, the X-ray energy and intensity corresponding to the applied voltages and current of the X-ray tube correspond to slightly higher than conventional fluoroscopic levels. The X-ray tube is energized continuously during an exposure sequence. The most common practice before the system shown in FIG. 1 was proposed was to pulse the X-ray tube on and off and to read out the video camera and effect conversion to digital picture element (pixel) intensity values between exposures. By way of example, when X-ray tube pulsing was used, voltages in the range of 65 to 120 kilovolts were applied to the X-ray tube and tube currents were as high as 1000 mA. Thus, the method practiced in the FIG. 1 apparatus is less likely to result in the thermal rating of the X-ray tube being reached or exceeded.

As is known, for temporal image subtraction, a sequence of one or more mask images are made of the region of the anatomy that contains the blood vessels of interest. The mask images are made before an X-ray contrast medium such as an intravenously injected iodinated compound arrives in the region of interest. Typically, the contrast medium arrives in the region of interest anywhere up to 20 seconds after it has been injected. The imaging sequence is continued after the contrast medium enters the vessels in the region of interest and, possibly, for a short time after it has left and has been replaced by noniodinated blood. Thus, a sequence of television frames containing pre-contrast images followed by post-contrast images are obtained. The normal 1/30 of a second television frame time prevails. Typically, a sequence may contain a total of 20 images.

Figure 2:
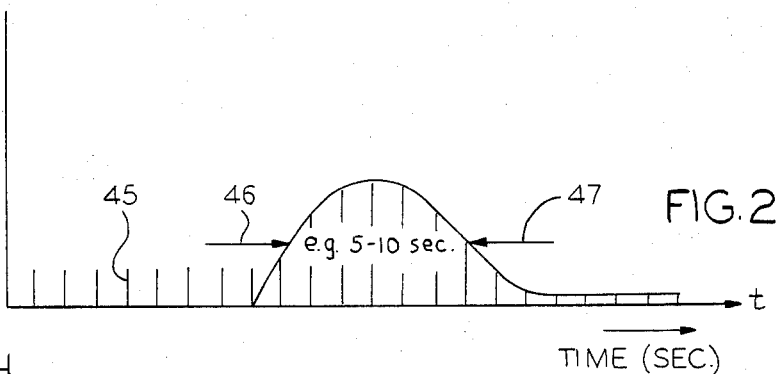
FIG. 2 is a typical plot of contrast medium concentration or projected intensity of contrast medium in a blood vessel versus time (t)

A typical plot of contrast medium projected intensity or concentration of the medium in the blood vessels of interest vs. time is depicted in FIG. 2. At time $t=0$ the X-ray contrast medium is assumed to have been injected and the X-ray tube is energized or turned on. The pre-contrast mask images are denoted by the short vertical lines such as the one marked 45. At $t_1$, contrast medium has begun to enter the blood vessel section or region of interest. The plot of its concentration rises with a sharp upslope and declines less rapidly. At time $t_2$ the contrast medium is substantially out of the region. The half-maximum points on the concentration curve are designated by the arrows marked 46 and 47. Typically, the elapsed time between the half-maximum points is on the order of 5–10 seconds. This time, however, may differ for different blood vessels such as renal, carotid, and coronary arteries.

Referring again to FIG. 1, one may see that the digitized images are output from ADC 19 to a logarithm look-up table 20 wherein the digital pixel signals are converted to corresponding logarithmic values before they are processed. The output of logarithm look-up table 20 feeds two 12-bit buses 21 and 22 which are the input buses to the two recursive filter channels which are used in the system. The one recursive filter channel contains a digital summer 23 that is input to a full-frame memory 24 and also labelled M1. The live video image is fed into one input of summer 23 through an attenuator 25 to which the legend KL has been applied to indicate that this attenuator multiplies the live image (L) pixel values by a coefficient K. The output 26 of frame memory 24 is fed back to another input of summer 23 through another attenuator 27. As indicated by the legend on attenuator 27, it multiplies the stored image pixel data S by the quantity $(1-K)$. The image frame number is designated by "n". Attenuators 25 and 27 are ganged and respectively introduce the transmission constants or coefficients of "K" and $1-K$. That is, a fractional part $(1-K)$ of the amplitude of the stored video signal output from memory 26 is applied to one summer 23 input and a fractional part "K" of the amplitude of the present or live video signal is applied to the other input of summer 23. Thus, if the value of K is increased, the proportion of the live video signal applied to the summer 23 increases and the proportion of the stored video signal applied to the summer decreases. Conversely, if "K" is decreased, a smaller portion of the live signal and a larger proportion of the stored signal are applied to the summer.

The summer 23, memory 24 and attenuators 25 and 27 constitute an infinite memory system in which a fractional amplitude portion of the sum of all previous or earlier image frames or frame signals are added to a fractional amplitude portion of the present or live video signal, the relative importance of a signal "n" frames previous to the live frame being determined by the value of "K". The feedback process results in noise cancellation for reasons given earlier. When a sequence of signals representing image frames are summed in the foregoing manner, the result is a signal or set of image data identical to any one of the summed signals and of the same magnitude as the unattenuated live signal by reason of the fact that the sum of "K" and $(1-K)$ is always and must be unity. However, when random noise that is present in the video signal and varies from frame to frame, is summed, it tends to be cancelled or in any case is not reinforced as is the periodic frame video data.

The other or second recursive filter channel in FIG. 1 is comprised of attenuators 30 and 31, a summer 32 and another full-frame memory 33 which also has the legend M2. The recursive filter in this channel functions identically to the one described above except that the value of K is different in this channel and is designated as K' to indicate the difference. Although the recursive filters shown in FIG. 1 are structured slightly different than in the cited articles, they function in essentially the same way as the cooperating recursive filters depicted and described in the articles. There is a simultaneous input of the same video information to the input attenuators 25 and 30 of the respective recursive filter channels but the output signals on their respective output buses 28 and 29 differ in magnitude.

Before discussing the operating theory of the recursive filters in depth, one may note in FIG. 1 that the image data output from memories 24 and 33 constitute separate inputs to a digital subtractor 34. Corresponding pixels for the same frame coming out of memories 24 and 33 are subtracted and the resulting difference image data from subtractor 34 is inputted to a gain and offset introducing device 35 where the relatively low magnitude difference signal is altered so it will fill the full dynamic range of a television monitor that is used to display the difference image. In FIG. 1, the digital difference image data, after it is processed in gain and offset introducing device 35, is fed to a digital-to-analog converter (DAC) represented by the block marked 36. The analog video output signals from DAC 36 are supplied by way of a cable 37 to a television monitor 38 on whose screen 39 the contrast medium which defines a blood vessel such as the one marked 40 is displayed.

Figure 3:
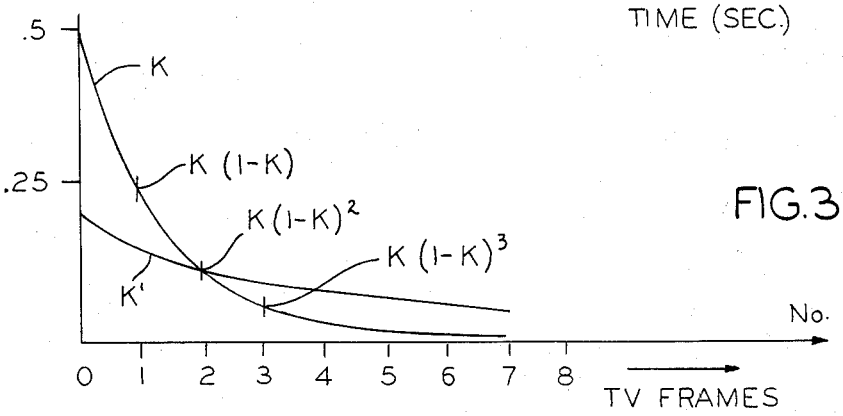
FIG. 3 is a plot of system response for two different recursive coefficients with respect to time expressed in terms of television (TV) frame times.

FIG. 3 illustrates the impulse response of recursive filters. Response is plotted against time which is expressed in terms of television frames for two different values, K and K', of the coefficient. It is assumed for the sake of demonstrating impulse response that in FIG. 3 a single television frame is input to either of the recursive filter channels. Essentially, the curves in FIG. 3 demonstrate the lag in television image brightness if only one bright view were inserted in a memory, repeatedly acted upon by $(1-K)$ and displayed. One may see that when the first TV image frame enters at frame 0, image intensity or brightness is maximum. Then for each recursive cycle related to successive frame times, brightness or image intensity in the memory declines exponentially. At the sixth frame in the FIG. 3 illustration, brightness is reduced almost to zero for the curve where the coefficient is designated by K. Thus, it will be evident that under operating conditions where a series of television frames are input to a recursive filter, the current or live frame will have the greatest weight in the memory and as one goes back in frames those frames have continuously decreasing weight. FIG. 3 also shows how the weight of a frame declines in a case where a coefficient is K' and K' is less than the coefficient K.

Figure 4:
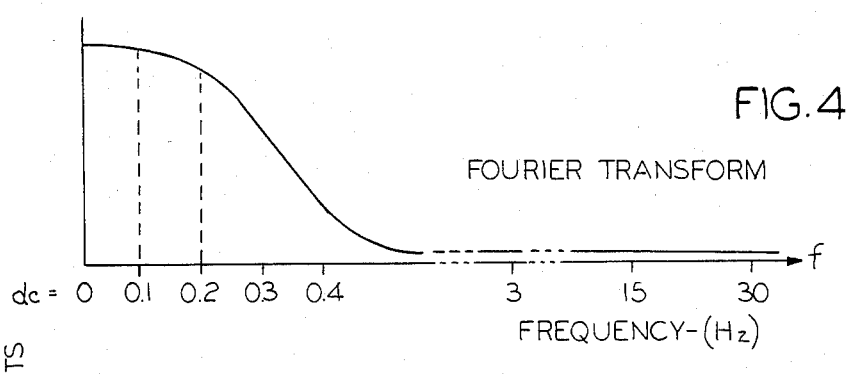
FIG. 4 is a Fourier transform resulting from transforming projected intensity of contrast medium from the time domain as in FIG. 1 to the frequency domain as in FIG. 4.

To further appreciate the principles underlying recursive filters, one may note again in FIG. 2 how the concentration of X-ray opaque medium in the bolus flowing through the blood vessel of interest is a function of time. By Fourier analysis, the plot in the time domain in FIG. 2 can be transformed to the frequency domain as in FIG. 4. FIG. 4 is a plot of signal amplitude, essentially the output from one of the memories 24 or 33 versus the frequency content of the time domain plot. Thus, in FIG. 2 the width of the curve at half maximum is typically 5 to 10 seconds. As is known, taking the reciprocal of the width of the curve in the temporal domain qualitatively expresses its magnitude in the frequency domain which in this case is 1/10 to 1/5 or 0.1 to 0.2 Hz. These points are designated on the frequency axis in FIG. 4. It will be evident then that in this analysis the frequency content of the signal or projected flowing contrast medium is primarily in the range of 0.1 Hz to 0.2 Hz. In FIG. 4, it will be evident that the signal at zero frequency is nonzero which is equivalent to saying that the curve has a dc component. Anything that does not move or change between successive images is represented by a positive magnitude at zero frequency and zero magnitude at all other frequencies. This lays the basis for cancelling or subtracting out everything that is constant among successive image frames such that only the variable due to contrast medium flow will remain. The subtraction process eliminates all structures that do not change between images, or expressed another way, has zero response at zero frequency or a zero response to dc. A requirement of all subtraction or filtering means which eliminate background is to have zero response to dc.

It should be noted in the FIG. 4 Fourier transform plot that for frequency components or harmonics that are very high, signal amplitudes are very low and are at the frequencies corresponding to background information and noise.

Figure 6:
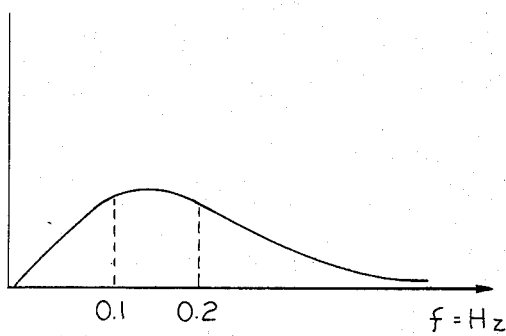
FIG. 6 is a plot illustrating ideal recursive filter output signal response relative to frequency.

Consider again the nature of temporal subtraction. A pre-contrast mask image is obtained and one or more successive post-contrast images are obtained. The mask is subtracted from any one of the post-contrast images. Any subtraction results in cancelling out materials or structures that have not changed from one image to the other. In this case, the structures in the body or object that are constant all cancel out in the difference images that are reckoned in the time domain but they can also be looked upon as cancelling out in the frequency domain. Suppose that the subtraction process is such that soft tissue and bone and anything else that is constant in the images are being subtracted out. Consider a signal resulting from something behind a stationary object. If there is no opaque medium flowing behind it or in front of it the same signal value will be obtained at all times. In other words, in the Fourier analysis of a stationary structure, a plot of signal in relation to time results in a constant signal and in the Fourier analysis, which is a function of frequency, the only frequency value will be zero. Thus, the Fourier transform in FIG. 4 demonstrates how frequencies of interest of the contrast medium bolus are distinguished from all of the high frequency contributing factors and also from stationary or constant objects which are at exactly zero frequency. A desirable situation to be obtained is illustrated in FIG. 6 where there is no system response at zero frequency, maximum response in the frequency range of interest where the particular bolus curve used for illustration is in the range of 0.1 to 0.2 Hz, and again, reduced or no system response to frequencies outside of this range. Truly ideal response cannot be obtained in recursive filter systems but is obtained in the matched filtering system which will be described after the theory and problems of recursive filter systems are fully elucidated.

It should be noted in FIG. 4 that there is a high response in the frequency band, 0.1 Hz to 0.2 Hz, of interest. Also note that if the response were to be larger in the high frequency range, this would amount to allowing more noise into the images. The high frequency noise is generally exhibited as speckle on the TV screen that results from frequencies much higher than the bolus frequencies. These high frequencies can be eliminated by constraining the filter frequencies to be not higher than the bolus frequencies.

In customary temporal subtraction, a pre-contrast mask image is subtracted from a post-contrast image to produce an image in which everything is substantially cancelled except the image of the contrast medium. The subtraction process is not quite as discrete in the two-channel recursive filter system of FIG. 1. The most recent image frames have the greatest weight in either of the memories 24 or 33 and the earlier images have less and less weight as previously explained in connection with FIG. 3. Thus, as the contrast medium bolus begins to appear, the contribution of the mask images in the memories diminishes and the contrast medium images begin to predominate. Nevertheless, suppose that a sequence of 30 images are obtained and filtered. As long as there is a zero response at zero frequency, no further subtraction is necessary. The summation of the 30 image frames becomes the final image. Hence, the summation of the series of frames is already a type of difference image even though it is not the result of a direct subtraction of a post-contrast image from a mask.

Figure 5:
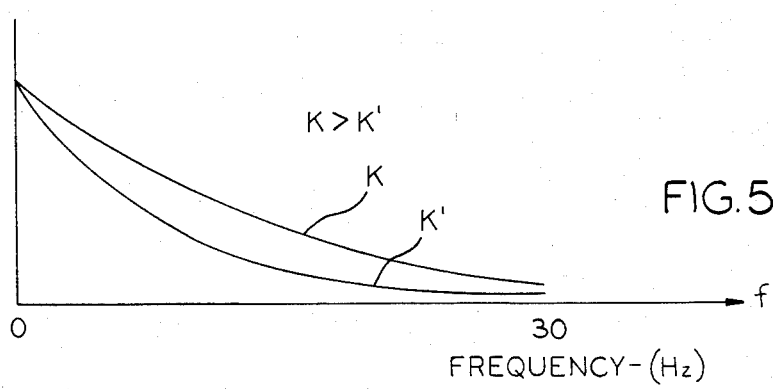
FIG. 5 is a plot of recursive filter output signal versus frequency for two different recursive filter coefficients.

FIG. 5 is a plot of recursive filter frequency response values for different coefficients versus frequency. These are the responses from the first channel wherein a coefficient of K is used and the second channel wherein a coefficient of K' is used. One may see that the signal values differ over most of their range but they are equal at zero frequency and again almost equal at a much higher frequency such as around 30 Hz. Thus, when the subtraction of the output signals from the respective recursive filter channels in FIG. 1 occurs in subtractor 34, pixels representative of image areas which are unchanged between successive images are cancelled out and noise that is represented by higher frequencies are also cancelled out as the result of subtraction. The difference signal is that which represents the contrast medium that is moving and exhibits a small range of frequencies. Hence, it will be evident that the signal processing system in FIG. 1 is essentially a bandpass filter that is unique as a result of it being characterized by cooperation of two separate recursive filter channels which each have different time constants.

It should be remembered that the shape of the contrast medium concentration versus time as in FIG. 2 will differ, depending on which blood vessels are involved and upon where the contrast medium is injected intravenously. Thus the frequency range of interest in the Fourier transform of FIG. 4 may be somewhat different and the coefficients K for emphasizing the frequency band of interest may also be somewhat different. In any case, however, the difference signals resulting from subtraction as in FIG. 5 for the different coefficients will be relatively small. Generally, one K value may be around 0.007 and the other around 0.03 so the differences between appearance of the signals coming out of the memories 24 and 33 may be relatively small. The difference image signal will always have less dynamic range than the signals from the individual recursive filter channels. The average output level from the subtractor 34 in FIG. 1 is zero if no contrast medium is present. Zero should correspond to the mid-gray region in the gray scale of the display so it is desirable to add a pedestal or dc offset back in and this is done with the gain and offset introducing device 35 in FIG. 1. Moreover, as indicated earlier, the signal must also be given some gain so it fills the full dynamic range of the television display device 38.

An inherent efficiency limitation present in the dual channel recursive filter scheme of FIG. 1 will now be discussed and the manner in which this inefficiency limitation is obviated with the new matched filter will then be discussed.

Figure 7:
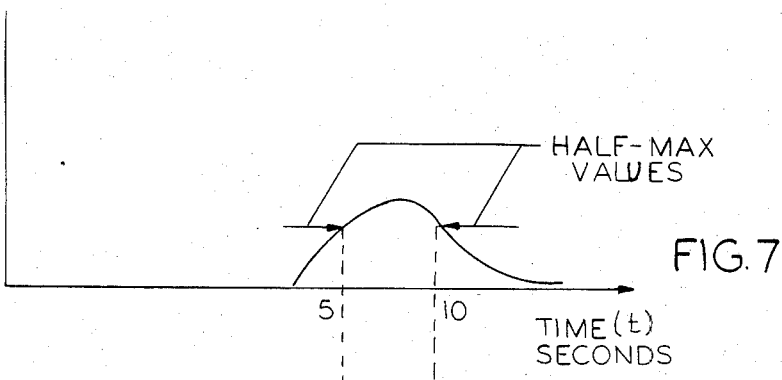
FIGS. 7, 8 and 9 are related and show, respectively, a typical plot of contrast medium projected intensity or concentration versus time in FIG. 7, the history or weight that previous images contribute to the present image in one recursive filter for a particular coefficient "K" as in FIG. 8; and, likewise the weight that previous images contribute to the present image for another coefficient, K'.
Figure 8:
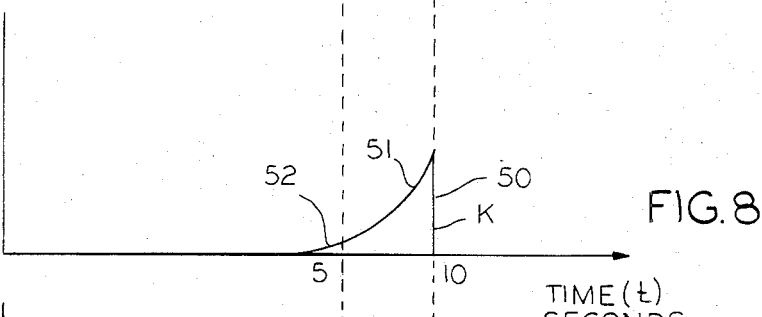
Figure 9:
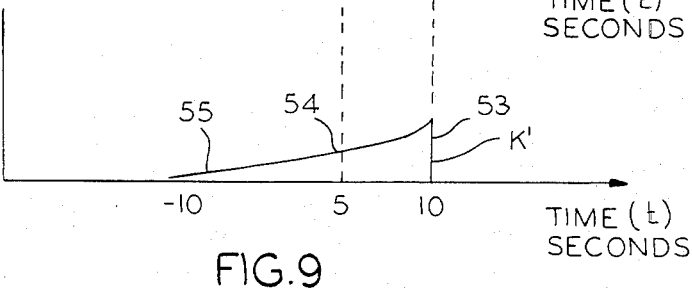

As a basis for this discussion, an illustrative contrast medium concentration versus time plot is repeated in FIG. 7. This is really the concentration that is represented in the projected X-ray images. The half-maximum points are again at about 5 and 10 seconds from initiation of contrast medium flow. FIGS. 8 and 9 depict the impulse response of the system where the value of the coefficient K in FIG. 8 results in a short time constant and the value of K' in FIG. 9 results in a relatively longer time constant. One may see in FIG. 8 that at 10 seconds the weight of the present incoming video frame in the memory in one channel would have the amplitude 50 and the contribution made to the image data such as at frames 51 going back to 52 would be less and less. Actually, the image frame in memory is the summation of all previous weighted frames. But in FIG. 8, all of the frames within the 5-10 second time interval would have some contribution from the X-ray contrast medium. In FIG. 9, at the time of ten seconds, the total signal magnitude of the memory in the other recursive channel having the slower time constant is the summation of all previous frames but weighted by the K' curve. For example, the video frame at 10 seconds is weighted by the value at 53, the frame at 5 seconds by the value at 54, etc. Thus, in FIG. 9, during the 5-10 second interval of interest, there is still some small contribution to the image resulting from pre-contrast exposures that have occurred in the time interval, in terms of frame times, from the frame designated 54 at 5 seconds going back to frames that still have minor significance such as the frame at the point marked 55. The important point is that during the 5-10 second interval of interest in this example, more than the pre-contrast contribution to the image in the memory associated with FIG. 9 is being subtracted out because there is a substantial amount of post-contrast contribution in the longer time constant channel where K' is used and subtraction results in producing the difference between the contrast medium values. Hence, the difference is smaller and the output signal from subtractor 34 is smaller, which is undesirable. For the sake of comparison, in general terms, where pre-contrast and post-contrast images are temporally subtracted as was most common prior to the recursive filter scheme, the difference signal might be assigned an arbitrary value of 10 for the sake of comparison and the noise level would typically be 1 such that the signal-to-noise ratio would be about 10. In recursive filtering for the same X-ray exposure intensities the useful difference signal might have a value of five on the same scale, a noise level of about 0.1 and a signal-to-noise ratio of 50. The idea of matched filtering is to preserve the signal level of conventional temporal subtraction while obtaining the noise reduction of recursive filtering. This would result in a signal-to-noise ratio of 10/0.1 or 100, an additional significant improvement over the recursive filtering case.

The new matched filtering method will now be described. Matched filtering is distinguished by its ability to cancel noise and everything else such as bone and soft tissue which remains constant in a succession of X-ray images such that the signal which remains is representative of only the X-ray contrast medium whose projected intensity varies with time over the duration of the bolus. A series of pre-contrast and post-contrast images are obtained. The images are combined in such a way that those having the greatest amount of contrast are weighted most heavily and as contrast or opaque medium intensity decreases in the actual image, the weight that is assigned to the images in the span of time in the summation decreases in proportion to the signal that results from the X-ray opaque medium. Basically, the first pre-contrast image obtained, in a sense, serves as a mask. In one mode, subsequent pre-contrast images are subtracted from the mask in succession and the resulting difference images are added to preceding images and are stored in a full-frame memory. Similarly, the post-contrast images have the mask subtracted from them and they are stored. Typically, a sequence of around 50 difference images are obtained, the earlier of which have no signal contribution from the contrast medium and the latter of which do have such contribution. The difference images are subjected to matched filtering after all of them in a particular sequence or run are obtained. Filtering involves operating on the pre-contrast and post-contrast difference images with a filter function for respective coefficients which are related to the magnitude of the curve that represents the projected amount or concentration of contrast medium in a blood vessel vs. time. The coefficients are really weighting factors for the respective difference image frames. The sum of the weighted difference images or more specifically, the signals representative of the sum of the picture elements (pixels) of the difference images constitutes the signal which drives the television monitor or display device on which the blood vessels whose interiors are defined by the contrast medium are exhibited.

The pre-contrast difference images resulting from subtraction of the mask image from the subsequent respective live pre-contrast images results in difference images in which anything that does not change is to be cancelled out. The same is true of the difference images that result from subtracting the first or mask pre-contrast image from the subsequent respective succession of post-contrast images. Noise and unchanged structure in successive images, corresponds, in a sense, to the dc component that would exist in the sum of the difference image signals if the filter function were not applied to the difference images prior to summation. Measures are taken to subtract out this dc component such that signal due to only that which is changing, namely, the X-ray opaque medium remains.

One thing that must be done to accomplish matched filtering is to express the projected bolus intensity plot as a function "h" of time "t", herein called h(t). This can be done, for example, by taking a series of X-ray images within the time interval between arrival of the contrast medium and departure of the medium from the blood vessel in the region of interest. This can be done with several patients and the results can be averaged. In this way, the projected intensity of the contrast medium as a function of time can be plotted. The plot can also be estimated for a single patient from a sequence of relatively noisy images as will be described in greater detail later in reference to FIG. 14. It should be recognized that the value of the function "h" or the coefficient or multiplying factor will be different for each image frame since the magnitude of the bolus plot varies with time.

Figure 10:
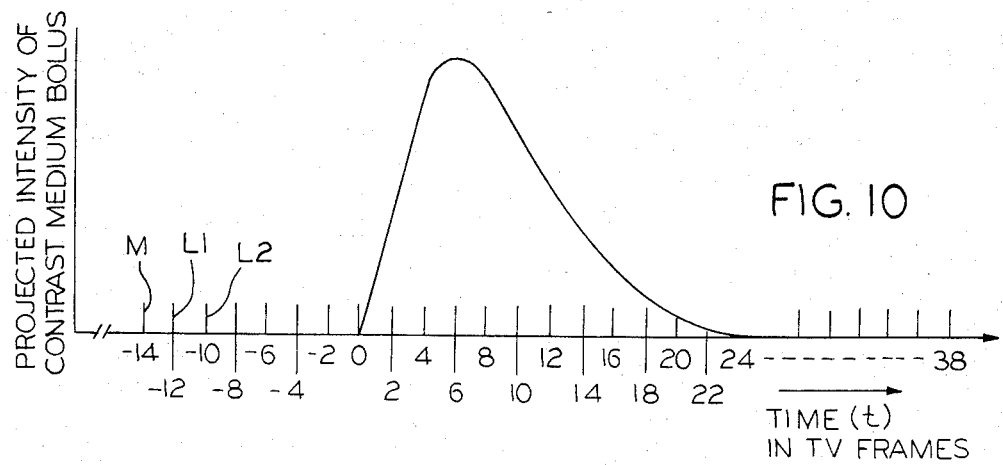
FIG. 10 is a repeat of a typical plot of contrast medium projected intensity or concentration in a blood vessel versus time in terms of TV frames.

Another representative projected contrast medium bolus plot is shown in FIG. 10. Assume now that the X-ray tube is projecting a beam through the region of interest of a body and that the X-ray tube is operating at fluorographic levels, that is, typically at less than 100 kV applied voltage and a tube current of about 5 mA. A sequence of images is to be obtained and subjected to matched filtering. Assume in FIG. 10 that the X-ray opaque medium has been injected and has not arrived in the blood vessels of interest as yet. Then, prior to minus 7 on the time scale (t) the X-ray source is turned on. At $t = -7$ a mask image "M" is obtained. Readout of the television camera target results in analog video signals representative of this mask image M. By referring to FIG. 12, a diagram of a matched filter system, one may see that the mask image and all other images are obtained by a television camera 65 viewing the phosphor 66 of the X-ray image intensifier 67 that produces the visible image on the phosphor of the body region through which the X-ray beam passes. For the time being, assume that the analog video signals representative of any image under consideration will be stored in the FIG. 12 system at least until a sequence of difference images are obtained as will now be discussed in reference to FIG. 10 again. Pre-contrast images and post-contrast images obtained subsequent to the mask image are called Live (L) images for convenience. For the purpose of matched filtering, a series of live images are acquired. such as those marked L1 and L2 in FIG. 10, during the pre-contrast period. In the preferred mode of operation, live image L1 is subtracted from the mask M and the resulting difference image is stored in analog signal format in a suitable storage device in the FIG. 12 arrangement which will be discussed in greater detail later. Similarly, the signals representative of the live image L2 are subtracted from the mask M and stored. This procedure is carried on throughout the whole pre-contrast period and through and past the post-contrast range, in terms of time, in FIG. 10. In other words, every live image, L, is subtracted from the mask, M, and the difference image is stored in analog video signal form. In a practical case, difference images are obtained at a rate of about 5 per second. A higher rate, as high as 30 frames per second, could be obtained if desired. The images can be generated using continuous X-ray exposures in which case the video camera is read continuously at 30 video frames per second. Using integration within a digital video processor, contiguous video frames can be added to reduce the image rate presented to the storage device. For example, every 6 consecutive video frames could be added together, resulting in a net image rate of 5 images per second. The images could also be generated using pulsed X-ray exposures if desired. A sampling rate of 5 images per second is probably all that is required. This would yield about 50 difference images over the time interval of the bolus.

What has been described thus far in reference to FIG. 10 can be expressed symbolically by stating that each difference image is represented as $D_i$ and that the sequence of them is: $L_1$-M, $L_2$-M, $L_3$-M, ... $L_n$-M where "n" is the nth or last image taken and used in the sequence, L is the present or live image, and M is the mask.

As stated earlier, the filtered image is the sum of all of the difference images, $D_i$, after they have been acted upon by the respective functional values $h_{i(t)}$ of the bolus curve at the time the difference image was obtained. Expressed symbolically:

$$\text{Filtered Image} = \Sigma_i h_i D_i \qquad (\text{Eq. 1})$$

remembering that $h_i$ has a different value or is a different coefficient for each $D_i$.

The preceding expression can be expressed in another way as follows:

$$\text{Filtered Image} = \Sigma_i h_i (L_i - M) \qquad (\text{Eq. 2})$$

The preceding equation can be expressed in another way:

$$\text{Filtered Image} = \Sigma_i h_i L_i - (\Sigma_i h_i M). \qquad (\text{Eq. 3})$$

The significance of the two equivalent expressions in the next two preceding paragraphs is to show that the filtering steps can be broken into two summations such that the matched filter can be represented as a summation of the live images, (the first term of equation 3, minus the summation of the mask images, the second term of equation 3.) In equation 2, one gets a significant reduction in noise in the first term because noise is random and it is different between each of the image frames. In equation 3, in the second term the noise is identical in each frame so the second term of equation 3 does not result in any noise reduction. Thus, it will be evident that the mask image in equation 3, that is, the second term, is in the nature of a dc component or something that remains constant between images in that it is common to each of the series of pre-contrast and post-contrast images. This is similar to structures such as bone and soft tissue that are common and constant in all unsubtracted images in the sequence. In equation 2, it will be evident that it is not just bone and tissue but a fixed noise pattern of the mask image itself that remains constant or immobile in all of the sequence of images. An incident of matched filtering is that these constant contributions to the images are subtracted out and that is done by ensuring that the dc response of the matched filter system is zero.

Figure 11:
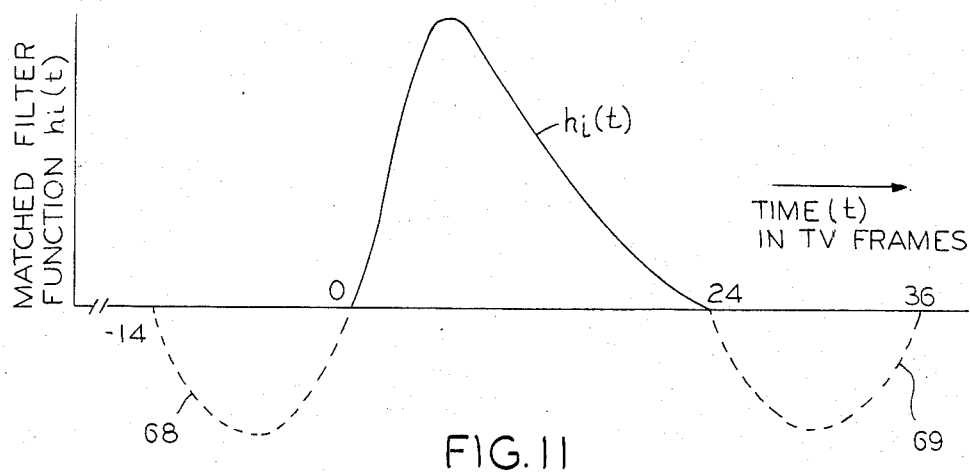
FIG. 11 relates to FIG. 10 and is a plot of a matched filter function versus time for one matched filter modality or embodiment in accordance with the invention.

Consideration should now be given to the matched filter function $h_i(t)$ which is typified in FIG. 11 and relates to the bolus or contrast medium intensity plot in FIG. 10. FIG. 11 shows how the part of the plot of the matched filter function, h, vs. time that is above the abscissa corresponds in configuration to the bolus curve. What this amounts to is that any image obtained at any time, t, during the image sequence after the bolus arrives in the region of interest will be weighted by the value of the ordinate, $h_i$, corresponding to the same time in the FIG. 11 filter function plot. In other words, the function, h, has a different value for every image frame. To have a filter function that has a dc component equal to zero is equivalent to saying that the sum of the filter function values all add up to zero. Consider how the filter function can be matched to the bolus and still ensure that the sum of the filter function values equals zero.

The bolus function as seen in FIGS. 10 and 11, is always larger than 0. The bolus function in FIG. 10 indicates the amount of X-ray contrast medium that is in the X-ray beam or projected at each image frame time. If it were not for the fact that h(t) must equal zero to eliminate all background information from the images, a filter function like that which is above the abscissa or positive in FIG. 11 would be satisfactory. However, the mask and live pre-contrast images have the same background as the post-contrast images due to noise, soft tissue and bone, for instance. The bolus function in FIG. 11 is always larger than zero. If a function is always larger than zero or equal to zero, its summation of values cannot equal zero. To get around this situation, negative-going functions such as those embraced within the curved dashed lines 68 and 69 are used. These curves 68 and 69 span over a time when the mask image is present but there is no bolus. The areas under curves 68 and 69 below the abscissa or negative region are equal to each other. In other words, the pre-contrast images and later than or after post-contrast images are multiplied by filter functions, respectively, represented by the negative-going ordinates of curves 68 and 69. On first impression, it would appear that this would bring about complete cancellation of all signals. This does not happen. The reason is that there is no X-ray opaque medium in the image representing signals present during the times when the filter function in FIG. 11 is negative. In effect, $h_t$, where $h_t$ is negative, is being multiplied by zero and similarly, at all times up until the bolus arrives, there is zero signal present due to the X-ray opaque medium. Once the opaque medium arrives, the filter value is positive as is the bolus so the bolus or contrast medium signal is in all cases being multiplied by positive values of h(t). It is not necessary that both negative-going lobes be equal to each other but rather that the total area of any negative-going portion(s) be substantially equal to the area of the positive-going portion. Expressed another way, the sum of all the coefficients used, both positive and negative, must substantially equal zero. This insures that the dc response of the filter is zero, or equivalently, the all static structures in the image sequence are eliminated in the final image. The operator may choose to apportion more of the negative-going portion of the filter to the pre-contrast or after post-contrast images, depending upon such things as patient motion. As indicated earlier, the hardware for conducting the matched filter process has a provision for storing the sequence of images on disk and applying the filter function to the images can take place after the whole image sequence is obtained. As will be evident when the hardware for matched filtering is described in greater detail in connection with FIG. 12, that the images can be displayed in sequence whether they be difference images obtained by subtracting live images from the mask image or whether they be unsubtracted images at the time. It is, of course, necessary to match the filter function $h_{i(t)}$ and the images stored on the disk. For example, one could obtain correspondence between the peak of the filter function and the image containing maximum contrast intensity and other images would match. By displaying the sequence of images, however, a bench mark can be obtained. For instance, the bench mark may be the first image in which contrast medium appears or it could be the image wherein the contrast medium exhibits peak intensity. The frames can be given serial numbers, 0 through 50, for example, which allow the user to make positive identification of the peak contrast intensity frame if that is the chosen bench mark. By way of an operator's console which will be discussed in connection with FIG. 12, the bench mark frame number can be inputted to a microprocessor which is used in the system for the microprocessor to match the stored filter function with the stored image data.

Figure 12:
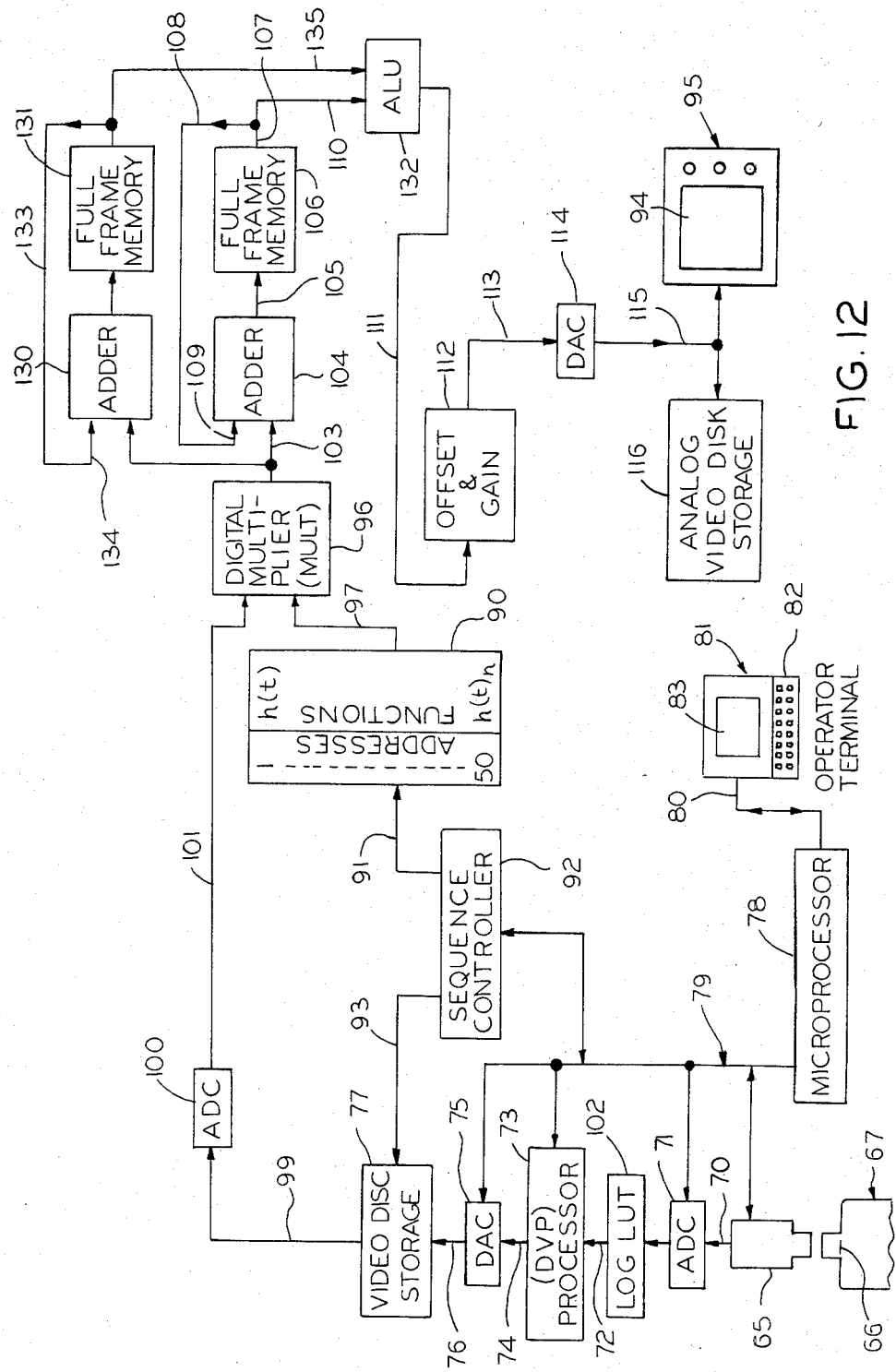
FIG. 12 is a block diagram of a system for acquiring X-ray images, performing matched filtering in accordance with the invention, and displaying a resulting X-ray image.

Discussion of the theory underlying matched filtering of X-ray images will be suspended for the moment to discuss hardware with which matched filtering is conducted. The basic hardware is shown in FIG. 12. The image intensifier 67 in the lower left region of FIG. 12 is similar to the intensifier 12 in FIG. 1 and provides on its phosphor 66 the optical version of each X-ray image. The X-ray tube is not shown in FIG. 12. However, assume that the tube will usually be operated at fluoroscopic current and voltage levels such as 5 mA and an applied voltage of under 100 kV. The X-ray beam is projected continuously beginning a short time before the first mask image M is obtained and remains on for a sequence of 50 or even more television image frames corresponding to X-ray images acquired over the pre-contrast period, at least the post-contrast period and possibly the after post-contrast period. In any case, the television camera 65 converts the image to corresponding analog video signals which are conducted by way of a cable 70 to an analog-to-digital converter (ADC) 71. ADC 71 samples the analog video waveform and converts it to a succession of digital numbers whose values correspond to the intensities of the picture elements (pixels) that compose the image. Typically, the digital values have a width of 8 bits. These values are converted to corresponding logarithm values with a look-up table (LUT) 102. The logarithmic digital values which correspond to the intensities of the pixels that compose the X-ray images are conducted by a bus 72 to the input of a processing circuit, which, for convenience, is called a digital video processor (DVP) and is represented by the block marked 73. DVP 73 is a versatile device that can operate on and manipulate data in various ways. Further, it has at least two full video frame memories configured in such a way that contiguous video frames can be integrated into either or both memories. The DVP also has digital circuitry capable of subtracting one memory from either the other memory or the live incoming video signal and additional circuitry to add a gain and offset to the resultant difference image. The DVP can also convert unsubtracted digital images, integrated or not integrated, into a video signal using the DAC. In one mode of operation, the digital data representative of the mask image, M, which is the first image obtained in a sequence, is stored in a memory of DVP 73. All subsequent live pre-contrast and post-contrast images in the sequence then have the mask image value subtracted from them in succession to produce a series of difference images, $D_i$, or, in fact, the digital data for such images. These digital data are output on a bus 74 from DVP 73 and are input to a digital-to-analog converter (DAC) 75 wherein the digital pixel signals are converted again to analog video signals that represent the individual difference images. The data representative of the respective difference images are input by way of a cable 76 to a video disk recorder or storage symbolized by the block marked 77. Output of recorder 77 is to an ADC 100. DAC 75 video disk storage device 77 and ADC 100 could be replaced by a digital storage device, not shown, if desired. A processor that includes the various converters and arithmetic logic units for performing these functions is illustrated in the co-pending application of Andrews, et al, Ser. No. 321,307, filed Nov. 13, 1981, now U.S. Pat. No. 4,449,195 assigned to the assignee of this invention. The main point of what has been said thus far is to establish that for one matched filtering mode the sequence of pre-contrast and post-contrast difference images are stored sequentially in analog video signal format in video disk storage 77.

It may be noted here also that for an alternative matched filtering procedure, the mask image and the subsequent live pre-contrast and post-contrast images may be fed directly to video disk storage 77 or alternative digital storage device, if desired, without previously performing the subtraction process in which case raw images are stored rather than difference images.

All of the timing of the hardware in FIG. 12 and data manipulation control is performed by a computer based on a microprocessor, represented by the block marked 78. The microprocessor bus 79 couples to various of the components just discussed for the purpose of providing synchronizing and control signals to them.

The microprocessor is suitably linked by way of a bus 80, including suitable interfaces, not shown, to an operator terminal 81 which has a keyboard 82 that provides for operator interaction with the system. The terminal also has a video display screen 83.

The system in FIG. 12 includes a coefficient or function generator which is preferably a random access memory (RAM) 90 in which the respective filter function values h(t) related to corresponding image frame times are stored. Various filter functions are contemplated. Any one may be selected by the operator using the keyboard 82 of the terminal 81 to cause microprocessor 78 to load a filter function into RAM 90. As indicated earlier, further experience with the matched filtering system may indicate that the filter function should be modified to obtain a closer match with the bolus intensity versus time plot. For instance, experience may demonstrate that the bolus dynamics for blood vessels in different organs of the body may be slightly different than what is presently considered to be a generalized bolus curve based upon plotting projected contrast medium intensity against time for a variety of patients and then correcting the plot so it is representative of the average patient with small departure from the mean. In any case, the various filter function values for the respective image frames in a sequence are stored in RAM 90 which may be considered a generator of coefficients corresponding to function h(t). RAM 90 has an address input bus 91 which is sufficient for addressing something on the order of 50 or more filter function values h(t) in sequence. In one mode of operation, the filter function values corresponding to the times at which the respective image frames are obtained must be coordinated or synchronized with output of such frames from video disk storage 77 in order to perform the matched filter multiplicative process. For this purpose, a controller 92 is provided. Besides having address bus 91 connedting it to RAM 90, it has another bus 93 coupling it to video disk storage device 77 for controlling output of the device. As indicated earlier, before the matched filtering process begins, the filter functions stored in RAM 90 must be coordinated with the difference image frames to which they relate. Also as indicated earlier, prior to initiating the matched filtering process in the first or preferred mode, the stored difference images are displayed on the screen 94 of a television monitor 95 which is shown in the far right region of FIG. 12. Assuming for the moment that such display can be effected, it provides the possibility of the operator finding a bench mark or image number whose corresponding image, for example, indicates maximum contrast medium such as the peak of the bolus plot in FIG. 10. The operator then uses keyboard 82 to input this number to the microprocessor 78 which causes the video disk storage 77 to be driven to coordinate the corresponding image number with the filter function h(t) that applies to that particualr difference image frame. After coordination is accomplished, the matched filtering process can be started. Matched filtering involves the step of multiplying the mask, M, and live, L, images in succession with the value of the function h that applies to the particular image. This multiplication process is carried out in a digital multiplier 96 that has a bus 97 for receiving the function $h(t_i)$, where "i" is the image number, from the addressed location in RAM 90. In an actual embodiment, the functions are expressed in 8-bit digital words and thus, bus 97 may be an 8-bit bus. The other input bus to digital multiplier (MULT) 96 supplies the digital pixel values corresponding to the analog video difference image frames that are stored in video disk storage 77. Output line 99 from video disk storage 77 is input to an analog-to-digital converter (ADC) 100 wherein the analog video frame data is converted to digital pixel format again. The digital pixel signal output from ADC 100 is supplied by way of the 8-bit bus 101 to MULT 96 where the difference image pixel data are multiplied in synchronism by the filter function value which applies to the particular frame going through. A bus 103, which is preferably 16 bits wide, couples the output of MULT 96 to one input of an adder or summing device 104. The output bus 105 from adder 104 is input to a full frame digital memory 106. The first difference image, $D_i$, after having been multiplied by filter function, h, goes through the adder 104 and into frame memory 106. The output bus 107 from memory 106 feeds in two directions, one of which is a 16-bit feedback bus 108 which couples the output of memory 106 to another input 109 of adder 104. Adder 104 and memory 106 cooperate to add the present difference image from multiplier 96 to the summation of the previous images that are stored in frame memory 106. In other words, each difference image in the sequence is acted upon by its filter function and then summed with all the images in the sequence such that the final summation is accrued in frame memory 106. The process of summing the successive images results in a substantial increase in the signal that corresponds to the amount of contrast medium projected relative to any noise signal. Recall also that the filter function plotted in FIG. 11 resulted in reducing the dc component of the accumulation of images to zero which means that everything that has not changed between the succession of images is eliminated and all of the signals in terms of pixel values is retained.

The summed image in frame memory 106 is displayed on the screen 94 of television monitor 95. Output bus 107 from the frame memory is coupled to a bus 110 that is input to an arithmetic logic unit (ALU) 132 which can be considered as simply passing the image data through in the mode of operation being described. The output bus 111 for ALU 132 is input to an offset and gain introducing circuit 112 which provides offset to the image signal so that the middle region of its gray scale corresponds to the middle region of the television monitor dynamic range. Gain is introduced to assure that the full dynamic range of the television monitor will be used. In any event, the digital signal output from circuit 112 on bus 113 is input to a digital-to-analog converter (DAC) 114 which converts the digital signals representative of the image pixel intensities to analog video signals again for being inputted by way of a cable 115 to television monitor 95 for driving the monitor. The video signals may also be stored on another analog video disk storage device 116 which makes the blood vessel image information available for future display on monitor 95.

In an actual embodiment, the digital pixel signals that are output from the full frame memory 106 for display are 16-bit words and bus 110 is a 16-bit bus. In the offset and amplifying circuit 112, the 8 least significant bits are clipped, thus leaving 8-bit words for input to DAC 114. 8-bit words are sufficient to fill the full dynamic range of the video monitor 95, and, of course, as those skilled in the art know, a television monitor cannot possibly display an image over a gray scale range as great as would be obtainable with 16-bit words. 8-bit words provide 256 gray scale gradations which exceeds the number of gradations that the eye can perceive.

The matter of how the system is effective to reduce noise and eliminate everything in the final image that is constant or unchanging in the succession of images while letting the signal representative of the contrast medium remain will now be discussed. Consider FIGS. 10 and 11 again. When the digitized mask image is subtracted from the succession of pre-contrast live images the difference between any one of the live images and the mask will be small. When the first digital difference image gets into the frame memory 106, some of its pixels may have slightly positive or slightly negative values due to noise and possibly some other residuals due to the subtraction process. When many of the live pre-contrast images and the mask image are subtracted and entered into the memory the noise and everything that is constant in the images essentially has an average brightness value of zero or it is of a uniform shade at least. When the subsequent live post-contrast difference images are added to the summation in the full-frame memory, the averaging process continues and the contribution made by noise to the signal during the bolus time still has an average of essentially zero. As indicated, of course, a difference image will never be zero everywhere. It will always have a noise level attached to it. That is, the values will be around zero and in some cases the value of an individual pixel will be zero but the whole image will not be zero uniformly so by adding the functional values defined by the dashed lines 68 and 69 in the function plot of FIG. 11 the multiplicative factor or coefficient has a value but it acts on an average value of zero so nothing is being added or subtracted and there is no reduction in signal due to the bolus. By looking at the pre-contrast difference images as frames whose average value is zero but whose pixel values may be at various levels one may see that when whatever the value is is multiplied by a function of coefficient h(t) some true values result and a modified frame results. This would be everything that is constant in the pre-contrast frames. What is multiplied is principally noise as all the constant structure has been subtracted out because of the differences between the mask and live images having been taken. So when all of the pre-contrast and post-contrast produce images resulting from successive multiplications by the coefficients are summed that is sufficient to subtract out of the final image that which is pre-contrast, post-contrast and after post-contrast noise.

In the FIG. 11 case, the post-contrast images data are multiplied by coefficients proportional to h at times (t) that register with or are related to the post-contrast image that is acquired at the corresponding time (t). The pre-contrast images and after-contrast images are multiplied by coefficients whose values are equivalent to the functions represented by the curves 68 and 69, respectively, and these coefficients are selected so that the sum of all of the coefficients will equal zero substantially.

$$\text{Filtered Image} = \Sigma h_i L_i - \Sigma h_j M_j \quad \text{(Eq. 4)}$$

Figure 13:
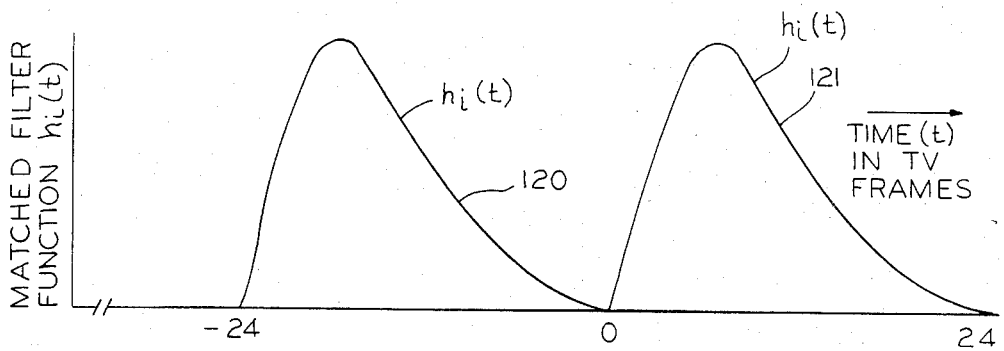
FIG. 13 relates to FIG. 10 and is a plot of an alternative matched filter function modality or embodiment in accordance with the invention; and, FIG. 14 is a plot showing how brightness or intensity of a selected region of interest in a sequence of unsubtracted images might vary from image to image, this figure being used to explain one way in which a filter function h(t) can be determined for use in a matched filter system.

Equation 4 indicates a matched filtering procedure that will now be discussed in reference to FIG. 13 primarily. The procedure associated with this figure is to generate one filtered image that occurs before the contrast medium arrives as one term of the equation and another that occurs after the contrast medium arrives as another term. The images that result from the respective summations are then subtracted from each other to produce a difference image in which everything that is constant, or the dc component, is reduced substantially in intensity. The two matched filter function plots or curves 120 and 121 are identical. In this case, a sequence of pre-contrast or, basically, mask images are begun at a time, t, corresponding to a television frame number that is arbitrarily designated as frame −24. A sequence of such frames are obtained at 5 frames per second, for example. For this mode another adder 130 and another memory 131 are used. The pre-contrast image data are operated on by the filter function $h_i(t)$ in digital multiplier 96 in FIG. 12. The digital data, would of course, be input on bus 101 to digital multiplier 96 and the filter function would be input on bus 97 as in the previously discussed embodiment. It is not necessary that the filter used for the pre-contrast images be the same as that applied to the post-contrast images. It is important, however, that the sum of the coefficients applied to the pre-contrast images be equal to the sum of the coefficients used for the post-contrast images. This insures upon the subsequent subtraction that the dc frequency response of the process is zero. The cumulative addition process would be carried on as before by the successive feedback from the output of frame memory 106 to an input 109 of adder 104. The image finally filling frame memory 106, for example, would not be a difference image at this juncture but would be a summation of pre-contrast mask and live images acted upon by the filter function. The contents of the frame memory would be represented by the second term ($\Sigma h_j M_j$) of Equation 4. In other words, the contents of the memory would represent everything that is constant in the sequence of images prior to arrival of the contrast medium bolus. Noise would be reduced somewhat because of it being averaged among the succession of images.

In this mode, the user keeps the television screen 94 under observation. Up to this point, a rather uniform light gray background would be appearing on the television screen. After about 24 image frames, in the FIG. 13 example, or at time 0 approximately, the bolus will have arrived in the vessels in the X-ray beam field. At this time, a change in intensity on the display screen is noticed and the operator presses a key on keyboard 82 that terminates accumulation of the image data in the one full frame memory 106. The sequence of post-contrast images is multiplied by respective coefficients of the filter function using multiplier 96 again. At this time, however, the image summation pixel data is accumulated in the full frame memory 131 after using adder 130. The image represented by this data in frame memory 131 will, of course, include averaged noise, everything that remains constant in the sequence of images, and an emphasized signal content that is representative of the bolus intensity. Post-contrast frames are obtained until there is a noticeable disappearance of contrast medium on the television display screen which, in the FIG. 13 illustration, would be at about frame number 24 following time zero. The user then terminates the post-contrast sequence by appropriate keyboard action.

At this juncture, a pre-contrast summation of images acted upon by the filter function is in frame memory 106 and a post-contrast sequence of images acted upon by the same filter function is in frame memory 131. The next step is to subtract corresponding pixel signals representative of the pre-contrast mask sequence from the post-contrast bolus sequence using ALU 132. This takes out most of the noise and the dc component or that which remains constant from one image in the sequences to another. The contents of memories 108 and 131 are fed to ALU 132 for subtraction by way of buses 107 and 135. The remaining signal represents the intensity of the bolus by itself and this signal is supplied through the circuitry from the output of ALU 132 to television monitor 95 for display.

Earlier mention was made to a second approach to developing the matched filter function h(t) and it will now be discussed in reference to FIG. 14. It is potentially advantageous to use the data that will be used to generate the matched filtered image to also derive the bolus function plot h(t). This can be done by first selecting a region of interest point or small zone in a displayed post-contrast image of a vessel. The brightness of this point will be proportional to projected contrast medium intensity. The microprocessor is programmed to determine the brightness of this same point in each of the acquired and stored images. The brightness of this point will, of course, be different in the successive images obtained during the post-contrast or bolus period. The microprocessor can next fit this data to a smooth curve representative of h(t).

Figure 14:
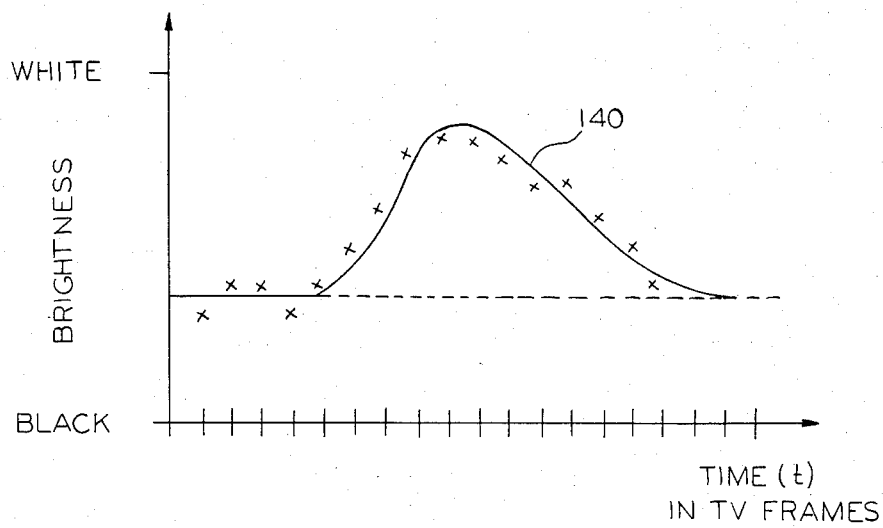

In FIG. 14, the brightness in said point for each image frame is indicated by respective points marked x. And the smooth curve 140 represents the bolus plot h(t) as related to brightness as determined by the measured brightness samples that are fed to the microprocessor. It is important to recognize that a point of interest can be identified in a relatively noisy raw image so prior match filtering is not required to aid in selecting this point. The microprocessor then loads the positive values of h(t) into coefficient generator or RAM 90 and it also loads any negative values, mentioned earlier, as selected by the operator into the coefficient generator 90.

One example of the function which the microprocessor is required to determine is the gamma variate which is as follows:

$$h(t) = At^B e^{-Ct} \qquad \text{(Eq. 5)}$$

The parameters A, B and C are chosen by the microprocessor so that h(t) best matches the measured brightness samples. A is the approximate peak brightness on the curve 140 representing the equation, B pertains to the rise time and C pertains to the decay time.

At various places in the foregoing description reference has been made to pre-contrast, post-contrast and after-contrast images as if each image at a time (t) consisted of single video frames obtained continuously at standard 30 Hz television frame rate. As previously indicated the X-ray source can be energized continuously during acquisition of the sequence of images. However, in some cases, integration of image data for several successive frames is desirable such as for 15, 10, or 7.5 frames and a time (t) can be related to each integrated image and to the coefficient or function h of the projected intensity of the contrast medium at times (t). It will be evident that if 15, 10 or 7.5 video frames are integrated, for example, pre-contrast, post-contrast and after-contrast images would be acquired every $\frac{1}{2}$, $\frac{1}{3}$ or $\frac{1}{4}$ second respectively. This is tolerable because the image acquisition intervals are still short when compared to the typical time of about five to 10 seconds between the half-maximum ordinates of the projected bolus intensity plot and a sequence of 50 or more integrated images can still be obtained in a relatively short X-ray exposure time.

Besides operating in the continuous video or integrated video modes where the X-ray source is continuously energized, operating in the pulsed X-ray beam mode is also permissible. In this case, the X-ray source is pulsed on and off cyclically to obtain individual frames. When no integration is desired the respective images in a sequence can be acquired during each television frame time when the source is on and the frame times between pulses can be used to scrub the target of the video camera to remove any residual signal due to the previous exposure. As is known, scrubbing involves electron beam scanning of the video camera target while no video signal is being read out. When integration is desired, several successive video frames are added to produce individual images in the sequence. Frame times between each successively that are integrated can be used to scrub the target.

Although approaches to matched filtering have been described in detail, such description is intended to be illustrative rather than limiting, for the matched filtering methods can be variously performed and are to be limited only by interpretation of the claims which follow.

We claim:

1. A method of imaging a blood vessel in a body where the period before a bolus of X-ray contrast medium arrives in the vessel is designated the pre-contrast period, the period during which constrast medium is flowing in the vessel is designated the post-contrast period and the period following the latter when the medium has left the vessel is designated the after-contrast period, and where an X-ray source, when energized, projects a beam through a body to produce X-ray images and means including a video camera are operative to produce data representative of the images, the method including the following steps:

during said pre-contrast period, acquire an initial mask X-ray image and an additional sequence of pre-contrast images and take the difference between logarithmic data representative of the mask image data and logarithmic data representative of the respective additional images and store the resulting sequence of pre-contrast difference image data, when the contrast medium arrives in the vessel, start to acquire an additional sequence of post-contrast and after-contrast images and take the differences between logarithmic data representative of the initial mask image and logarithmic data representative of the additional post-contrast and after-contrast images and store the resulting sequence of difference image data, multiply the sequence of pre-contrast, post-contrast and after-contrast difference image data by respective coefficients, the coefficients by which the post-contrast difference image data are multiplied being proportional to the projected intensity, h, of the contrast medium bolus at time (t) and registered with the post-contrast difference images so that a selected one of the coefficients is applied to the corresponding post-contrast image containing maximum contrast medium, and the coefficients applied to the pre-contrast and after-contrast difference images are selected so that the summation of all coefficients equals zero or close to zero, and sum the results of the sequence of multiplications of coefficients and difference image data to produce a set of data representative of the contrast medium in the vessel.

2. The method as in claim 1 wherein said coefficients are determined by measuring projected intensity of contrast medium at a point in the vessel versus time over the interval during which contrast medium is present in the vessel of one or more human bodies into which contrast medium has been injected and that have been taken as representing a typical interval, then using coefficients that are proportional to the intensity at any time to multiply the data representing an image acquired at a corresponding time.

3. The method as in claim 1 wherein said X-ray source is energized continuously while the data representative of said mask, pre-contrast, post-contrast and after-contrast images are being acquired.

4. The method as in claim 3 wherein each of said images is acquired during an interval corresponding to a video frame time.

5. The method as in claim 3 wherein data corresponding to a plurality of successive video frames are integrated to produce each one of said acquired images in a sequence.

6. The method as in any of claims 1, 2, 3, 4 or 5 wherein the energization factors of said X-ray source are an anode voltage in the range of 55 to 100 kilovolts and a current in the range of 5 to 20 milliamperes.

7. The method as in claim 1 wherein said X-ray source is pulsed on and off and each of said images in said sequence are acquired while said source is on.

8. The method as in claim 1 wherein said X-ray source is pulsed on and off cyclically and the data acquired during several successive on times are integrated to produce the data representative of each of said images in said sequence.

9. A method of imaging a blood vessel in a body where the period before a bolus of X-ray contrast medium arrives in the vessel is designated the pre-contrast period, the period during which the contrast medium is flowing in the vessel is designated the post-contrast period and the period following the latter when the medium has left the vessel is designated the after-contrast period, and where an X-ray source, when energized, projects a beam through a body to produce X-ray images, and means including a video camera are operative to produce data representative of the images, the method including the following steps:

acquire a sequence of X-ray images starting at the beginning of the pre-contrast period and continuing through the post-contrast period, and convert the data representative of the images to logarithmic data, using the manner in which the projected intensity of the contrast medium at a point in an image of the vessel changes as a function, h, of time (t), multiply the data representative of the post-contrast images by respective coefficients that are proportional to the projected intensity of a contrast medium, h, at time (t) registered with the post-contrast images so that a selected one of the coefficients such as the maximum coefficient is applied to the post-contrast image containing peak contrast, sum the results of the respective multiplications and store the resulting data, multiply data representative of the respective pre-contrast and after-contrast images, if any, by respective coefficients selected so that the difference between the sum of the coefficients applied to the pre-contrast and after-contrast images and the sum of the coefficients applied to the post-contrast images is equal to zero or close to zero, sum the results of the respective multiplications and store the resulting data, and take the difference between the sum produced after said multiplying of the pre-contrast and after-contrast images data and the sum produced after said multiplying of the post-contrast images data to produce a set of data representative of an image of the contrast medium in the vessel.

10. The method as in claim 9 wherein said coefficients are determined by measuring projected intensity of contrast medium at a point in a vessel versus time over an interval during which contrast medium is present in the vessel of one or more human bodies into which contrast medium has been injected and that have been taken as representative of a typical interval, then using coefficients that are proportional to intensity at any time to multiply the data representing an image acquired at a corresponding time.

11. The method as in claim 9 wherein said X-ray source is energized continuously while the data representative of said pre-contrast, post-contrast and after-contrast images are being acquired.

12. The method as in claim 11 wherein each of said images is acquired during an interval corresponding to a video frame time.

13. The method as in claim 11 wherein data corresponding to a plurality of successive video frames are integrated to produce each one of said acquired images in a sequence.

14. The method as in any of claims 9, 10, 11, 12 or 13 wherein the energization factors of said X-ray source are an anode voltage in the range of 55 to 100 kilovolts and a current in a range of 5 to 20 milliamperes.

15. The method as in claim 9 wherein said X-ray source is pulsed on and off and each of said images in a sequence are acquired while said source is on.

16. The method as in claim 9 wherein said X-ray source is pulsed on and off cyclically and the data acquired during several successive on times are integrated to produce the data representative of each of said images in a sequence.

17. A method of imaging a blood vessel in a body where the period before a bolus of X-ray contrast medium arrives in the vessel is designated the pre-contrast period, the period during which the contrast medium is flowing in the vessel is designated the post-contrast period and the period following the latter when the medium has left the vessel is designated the after-contrast period, and where an X-ray source, when energized, projects a beam through a body to produce X-ray images, and means including a video camera are operative to produce data representative of the images, the method including the following steps:
    acquire a sequence of X-ray image frames over the pre-contrast period and at least over the post-contrast period and convert the data representative of said image frames to corresponding logarithmic data representative of the sequence of images, respectively,
    using the manner in which the projected intensity of the contrast medium changes as a function h of time (t), multiply the data, respectively, representing the sequence of pre-contrast, post-contrast and after-contrast images, if any, by a sequence of coefficients, the coefficients for multiplying the post-contrast images data being proportional to the projected intensity of the contrast medium h(t) registered with the post-contrast image so that a selected one of the post-contrast images such as the maximum coefficient is applied to the post-contrast image data containing peak contrast, and the coefficients by which the pre-contrast and after-contrast image data are multiplied are selected so that the sum of all coefficients equals zero or close to zero, and
    sum the results of the sequence of multiplications of coefficients and images data to produce a set of data representative of an image of the contrast medium in the vessel.

18. The method as in claim 17 wherein said coefficients are determined by measuring projected intensity of contrast medium at a point in a vessel versus time over an interval during which contrast medium is typically present in the vessel of one or more characteristic human bodies into which contrast medium has been injected, then using coefficients that are proportional to intensity at any time to multiply said data representing an image acquired at a corresponding time.

19. The method as in claim 17 wherein said X-ray source is energized continuously while the data representative of said pre-contrast, post-contrast and after-contrast images are being acquired.

20. The method as in claim 17 wherein each of said images is acquired during an interval corresponding to a video frame time.

21. The method as in claim 17 wherein data corresponding to a plurality of successive video frames are integrated to produce each one of said acquired images in a sequence.

22. The method as in any of claims 17, 18, 19, 20 or 21 wherein the energization factors of the X-ray source are an anode voltage in the range of 55 to 100 kilovolts and a current in the range of 5 to 20 milliamperes.

23. The method as in claim 17 wherein the X-ray source is pulsed on and off and each of said images in said sequence are acquired while said source is on.

24. The method as in claim 17 wherein said X-ray source is pulsed on and off cyclically and the data acquired during several successive on times are integrated to produce the data representative of each of said images in said sequence.

25. A method of imaging a blood vessel in a body where the period before a bolus of X-ray contrast medium arrives in the vessel is designated the pre-contrast period, the period during which contrast medium is flowing in the vessel is designated the post-contrast period and the period following the latter when the medium has left the vessel is designated the after-contrast period, and where an X-ray source, when energized, projects a beam through a body to produce X-ray images and means including a video camera are operative to produce data representative of the images, the method including the following steps:
    during said pre-contrast period, acquire an initial mask X-ray image and an additional sequence of pre-contrast images and take the differences between logarithmic data representative of the mask image data and logarithmic data representative of the respective additional images data and store the resulting sequence of pre-contrast difference image data,
    when the contrast medium arrives in the vessel, start to acquire an additional sequence of post-contrast and after-contrast images and take the differences between logarithmic data representative of the initial mask image and logarithmic data representative of the additional post-contrast and after-contrast images and store the resulting sequence of difference image data,
    select a corresponding point in the successive post-contrast images obtained while said contrast medium was flowing in said vessel and determine the intensities, h, at said point in each of the images and convert said intensities, h, to coefficients that are proportional to h at successive times (t), multiply the sequence of pre-contrast, post-contrast and after-contrast difference images data by respective coefficients, the post-contrast difference images data being multiplied by the coefficients corresponding to the time (t) at which the post-contrast images were acquired, the coefficients by which the pre-contrast and after-contrast difference images data are multiplied being selected so that the summation of all coefficients equals or close to zero, and sum the results of the sequence of multiplications of coefficients and difference images data to produce a set of data representative of the contrast medium in the vessel.

26. A method of imaging a blood vessel in a body where the period before a bolus of X-ray contrast medium arrives in the vessel is designated the pre-contrast period, the period during which the contrast medium is flowing in the vessel s designated the post-contrast period and the period following the latter when the medium has left the vessel is designated the after-contrast period, and where an X-ray source, when energized, projects a beam through a body to produce X-ray images, and means including a video camera are operative to produce data representative of the images, the method including the following steps:

acquire a sequence of X-ray images starting at the beginning of the pre-contrast period and continuing through the post-contrast period, and convert the data representative of the images to logarithmic data, select a corresonding point in the successive post-contrast images obtained while said contrast medium was flowing in said vessel and determine the intensities, h, at said point in each of the post-contrast images and convert said intensities to coefficients that are proportional to h at times (t), multiply the data representative of the post-contrast images by the coefficients respectively corresponding to the time (t), respectively, at which the post-contrast images were acquired, sum the results of the respective multiplications and store the resulting data, multiply data representative of the respective pre-contrast and after-contrast images, if any, by respective coefficients selected so that the difference between the sum of the coefficients applied to the pre-contrast and after-contrast images and the sum of the coefficients applied to the post-contrast images is equal to zero or close to zero, sum the results of the respective multiplications and store the resulting data, and take the difference between the sum produced after multiplying of said pre-contrast and after-contrast images data and the sum produced after multiplying of said post-contrast images data to produce a set of data representative of the contrast medium in the vessel.

27. A method of imaging a blood vessel in a body where the period before a bolus of X-ray contrast medium arrives in the vessel is designated the pre-contrast period, the period during which the contrast medium is flowing in the vessel is designated the post-contrast period and the period following the latter when the medium has left the vessel is designated the after-contrast period, and where an X-ray source, when energized, projects a beam through a body to produce X-ray images, and means including a video camera are operative to produce data representative of the images, the method including the following steps:

acquire a sequence of X-ray image frames over the pre-contrast period and at least over the post-contrast period and convert the data representative to said image frames to corresponding logarithmic data representative of the sequence of images, respectively, select a corresponding point in the successive post-contrast images obtained while said contrast medium was flowing in said vessel and determine the intensities, h, at said point in each of the post-contrast images and convert said intensities to coefficients that are proportional to h at times (t), multiply the data, respectively, representing the sequence of pre-contrast, post-contrast and after-contrast images, if any, by a sequence of coefficients, the sequence by which said post-contrast image being said coefficients that are proportional to h at times (t) corresponding substantially to the times at which said post-contrast images were acquired, and the coefficients by which the pre-contrast and after-contrast image data are multiplied are selected so that the sum of all coefficients equals zero or close to zero, and sum the results of the sequence of multiplications of coefficients and images data to produce a set of data representative of an image of the contrast medium in the vessel.

28. Apparatus for imaging a blood vessel in a body region in which vessel the quantity of X-ray contrast medium flowing therethrough is a function of time and where the period before the contrast medium arrives in the vessel is designated the pre-contrast period and the period during which the medium is present in the vessel is designated the post-contrast period comprising:

means for acquiring a sequence of X-ray image frames over the pre-contrast period and at least over the post-contrast period, converter means having input means coupled to said acquiring means and having output means, said converter means being operative to convert said images to data representative of the images, respectively, as the images are acquired, means having input means coupled to the output means of said converter means and operative to take the differences between the data representative of a mask image frame acquired at the beginning of the pre-contrast period and the data representative of subsequent images, respectively, acquired during the remainder of the pre-contrast period and during the post-contrast period, said means operative to take the differences having output means, storage means having input and output means, the input means being coupled to the output means of said means for taking the differences between said image frames and operative to store the data representative of the difference images, multiplier means having a plurality of input means and means coupling one of said input means to said storage means, said multiplier means being operative to multiply each of the difference images data by a coefficient that is proportional to the quantity of the contrast medium in the blood vessel at the time the image resulting in the difference image was obtained, said multiplier means having output means, means for storing said coefficients, said storing means having output means coupled to another of the input means of said multiplier means, means for controlling said storing means to provide to said multiplier means the coefficients corresponding to said difference images, respectively, summing means having input and output means, and means coupling the input means of the summing means to said output means of said multiplier means, said summing means being operative to sum the data resulting from the successive multiplications, television means and means coupling said television to said output means of the summing means for displaying the image represented by the summed data.

29. Apparatus for imaging a blood vessel in a body region in which vessel the quantity of X-ray contrast medium flowing therethrough is a function of time and where the period before the contrast medium arrives in the vessel is designated the pre-contrast period and the period during which the medium is present in the vessel is designated the post-contrast period comprising:

image acquiring means for acquiring a sequence of X-ray images over the pre-contrast period and at least over the post-contrast period, means coupled to said acquiring means for converting said images to digital data representative of said images in the sequence, respectively, storage means for said digital data having input and output means, the input means coupled to said means for converting the images, means for converting the images to corresponding logarithmic data, means for generating a sequence of coefficients that are each a function, h, respectively proportional to the projected intensity of the contrast medium at a point in the vessel at a succession of times (t), memory means having input and output means, said input means coupled to said generating means for receiving and storing said sequences of coefficients, multiplier means having plural inputs and an output means, one input coupled to said output of the image storage means and another input coupled to said output of the coefficient memory means operative to multiply the data representative of the pre-contrast images by the coefficients respectively, first summing means having output means and having input means coupled to said output means of the multiplier means and operative to sum the results of said multiplications and means coupled to said summing means for storing the resulting set of data, said multiplier means also operative to multiply the data representative of the post-contrast images, respectively, by said coefficients, second summing means having output means and having input means coupled to said output means of the multiplier means and operative to sum the results of the last mentioned multiplications and means coupled to said summing means for storing the resulting set of data, arithmetic performing means having input means for the stored summed pre-contrast and post-contrast image data and having output means, said arithmetic performing means being operative to take the difference between said sets of data in registry to obtain a final data set representing the contrast medium in the vessel, and means including television means coupled to the output means of said arithmetic performing means for displaying the image represented by said final data set.

* * * * *